United States Patent [19]

Gaugh et al.

[11] 4,007,170

[45] Feb. 8, 1977

[54] PHOTOGRAPHIC EMULSIONS CONTAINING METHINE DYES HAVING A 1H-IMIDAZO[4,5-b]PYRAZINE NUCLEUS

[75] Inventors: Wilbur Seth Gaugh, Webster; Donald Warren Heseltine, Rochester; David Michael Sturmer, Pittsford; John Paul Freeman, Rochester, all of N.Y.

[73] Assignee: Eastman Kodak Company, Rochester, N.Y.

[22] Filed: June 26, 1974

[21] Appl. No.: 483,336

Related U.S. Application Data

[62] Division of Ser. No. 388,867, Aug. 16, 1973, Pat. No. 3,936,308.

[52] U.S. Cl. .................... 260/240 E; 260/250 BC; 260/240.4; 260/240.6; 260/240.65; 260/240.7

[51] Int. Cl.² ............. C07C 471/04; C07C 401/06; C07C 403/06

[58] Field of Search ....... 260/240.6, 240.65, 240 E, 260/250 BC, 240.4, 240.7

[56] References Cited

UNITED STATES PATENTS

| | | | |
|---|---|---|---|
| 3,542,548 | 11/1970 | Mee et al. | 260/240 E X |
| 3,597,196 | 8/1971 | Jones et al. | 260/240 G X |
| 3,598,595 | 8/1971 | Mee et al. | 260/240.6 X |
| 3,632,808 | 1/1972 | Brooker et al. | 260/240.6 X |

*Primary Examiner*—Allen B. Curtis
*Attorney, Agent, or Firm*—J. G. Levitt

[57] ABSTRACT

Light-sensitive photographic emulsions are provided which feature at least one methine dye containing a silver halide sensitizing 1H-imidazo[4,5-b]pyrazine nucleus.

4 Claims, No Drawings

PHOTOGRAPHIC EMULSIONS CONTAINING METHINE DYES HAVING A 1H-IMIDAZO[4,5-b]PYRAZINE NUCLEUS

This is a division of application Ser. No. 388,867, filed Aug. 16, 1973, now U.S. Pat. No. 3,936,308.

This invention relates to polymethine dyes, and more particularly to photographic emulsions and elements containing these dyes.

It is, accordingly, an object of the invention to provide silver halide sensitizers or light absorbing dyes for photographic elements. Another object is to provide methods for preparing these new compounds and photographic materials thereof. Other objects will become apparent hereinafter from a consideration of the description and examples.

In accordance with one embodiment of this invention photographic emulsions are provided which contain a dye having a 1H-imidazo[4,5-b]pyrazine nucleus.

In another embodiment of this invention, photographic emulsions are provided which comprise at least one cyanine dye having two nuclei joined together by methine linkages, one of the nuclei being a 1H-imidazo[4,5-b]pyrazine nucleus, which is joined through the 2-carbon atom thereof to the methine linkage, and a second nucleus to complete the cyanine dye. Advantageously, the second nucleus of such dyes contains a heterocyclic nitrogen atom, and the methine linkage is part of a polyene chain containing an equal number of alternating single and double bonds, one terminal carbon atom of the polyene chain being the 2-carbon atom of a 1H-imidazo[4,5 ,b]pyrazine nucleus, the other terminal carbon atom of the polyene chain being in the second nucleus and attached to the heterocyclic nitrogen atom.

The second nucleus in these dyes can be either a sensitizing or a desensitizing nucleus. When the 1H-imidazo[4,5-b]pyrazine nucleus is combined with a second sensitizing nucleus the resultant dye is an excellent sensitizer of negative silver halide emulsions. When the 1H-imidazo[4,5-b]pyrazine nucleus is combined with known desensitizing nuclei as the second nucleus or when the 1H-imidazo[4,5-b]pyrazine nucleus contains strong electron withdrawing substituents, the dyes are useful desensitizers and spectral sensitizers for fogged, direct-positive emulsions.

As used herein and in the appended claims, "desensitizing nuclei" refers to those nuclei which, when converted to a symmetrical carbocyanine dye and added to a gelatin silver chlorobromide emulsion containing 40 mole percent chloride and 60 mole percent bromide, at a concentration of from 0.01 to 0.2 gram dye per mole of silver, cause, by electron trapping, at least an 80% loss in the blue speed of the emulsion when it is sensitometrically exposed and developed 3 minutes at 20° C. in Kodak developer D-19. Preferably, the desensitizing nuclei are those which, when converted to a symmetrical carbocyanine dye and tested as just described, essentially completely desensitize the test emulsion to blue radiation. Substantially complete desensitization as used herein refers to nuclei which, when tested as described above, result in at least about a 90%, and preferably more than a 95%, loss of speed to blue radiation. Nitro-substituted heterocyclic nuclei of the type used in cyanine dyes are typical desensitizing nuclei.

In another embodiment of the invention, photographic emulsions are provided which comprise at least one merocyanine dye wherein said dye comprises two nuclei joined together through an acyclic methine group which is part of a polyene chain containing an equal number of alternating single and double bonds, one of the terminal atoms of the polyene chain being the 2-carbon atom of a 1H-imidazo[4,5-b]pyrazine nucleus, and the other terminal carbon atom of the polyene chain being in a second heterocyclic ring and attached to an extracyclic carbonylic oxygen atom.

In a further embodiment of this invention, photographic emulsions are provided which comprise at least one cyanine dye wherein said dye comprises two 1H-imidazo[4,5-b]pyrazine nuclei joined together through a polyene chain containing an equal number of alternating single and double bonds, the terminal carbon atoms of the polyene chain being the 2-carbon atoms, respectively, of the 1H-imidazo[4,5-b]pyrazine nuclei.

In still another embodiment, a photographic element is provided wherein at least one of the emulsion layers contain a dye having the 1H-imidazo[4,5-b]pyrazine nucleus.

The new dyes of this invention include those represented by the following general formulas:

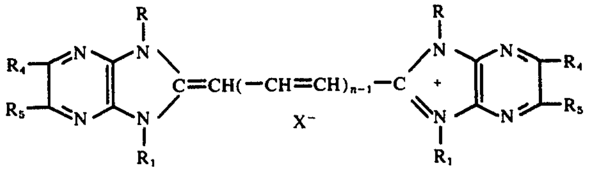

I.

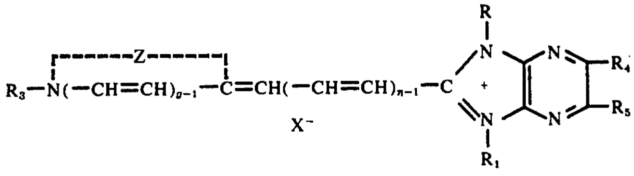

II.

-continued

III.

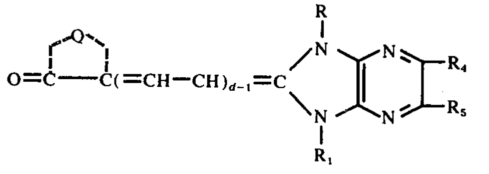

wherein *n* represents a positive integer of from 1 to 4, *g* represents a positive integer of from 1 to 2, *d* represents a positive integer of from 1 to 3; R, $R_1$, $R_3$, $R_4$and $R_5$ each represents a substituent independently selected from the group consisting of an alkyl group of from 1 to 12 carbon atoms, e.g., methyl, γ-sulfopropyl, isopropyl, butyl, sec-butyl, ω-sulfobutyl, dodecyl, β-hydroxyethyl, γ-hydroxypropyl, β-methoxyethyl, β-eththoxyethyl, allyl, benzyl, β-phenylethyl, β-carboxyethyl, carboxymethyl, γ-carboxypropyl, β-acetoxyethyl, γ-acetoxypropyl, carbomethoxymethyl, carboxyethoxyethyl, etc. and alkenyl substituents, preferably of 2 to 4 carbon atoms such as allyl, 1-propenyl, 2-propenyl, 1-butenyl, 2-butenyl and 3-butenyl, etc.; alkaryl substituents preferably of 7 to 12 carbon atoms such as benzyl and β-phenylethyl; and, aryl substituents preferably of 6 to 20 carbon atoms, e.g., phenyl, naphthyl, anthryl, 4-methoxyphenyl, p-tolyl, o-tolyl, 3,4-dichlorophenyl, 4-cyanophenyl etc.; $R_4$ and $R_5$ may also be a lower alkoxy group, halogen or a cyano group; $X^-$ represents an acid anion, e.g., chloride, bromide, iodide, thiocyanate, sulfamate, methyl sulfate, ethyl sulfate, perchlorate, p-toluenesulfonate, etc., Z represents the nonmetallic atoms required to complete a heterocyclic nucleus containing 5 to 6 atoms in the heterocyclic ring, which may also include, in addition to the hetero nitrogen atom, a second hetero atom such as an oxygen atom, a sulfur atom, a selenium atom, or a second nitrogen atom, such as the atoms required to complete a thiazole nucleus (e.g., thiazole, 4-methylthiazole, 4-phenylthiazole, 5-methylthiazole, 5-phenylthiazole, 4,5-dimethylthiazole, 4,5-diphenylthiazole, 4-(2-thienyl) thiazole, etc.); a benzothiazole nucleus (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, 5-hydroxybenzothiazole, 6-hydroxybenzothiazole, etc.); a naphthothiazole nucleus (e.g., α-naphthothiazole, β-naphthothiazole, 5-methoxy-β-naphthothiazole, 5-ethoxy-β-naphthothiazole, 8-methoxy-α-naphthothiazole, etc.); a thianaphtheno-7′,6′,4,5-thiazole nucleus (e.g., 4′-methoxythianaphtheno-7′,6′,4,5-thiazole, etc.); an oxazole nucleus (e.g., 4-methyloxazole, 5-methyloxazole, 4-phenyloxazole, 4,5-diphenyloxazole, 4-ethyloxazole, 4,5-dimethyloxazole, 5-phenyloxazole, etc.); a benzoxazole nucleus (e.g., benzoxazole, 5-chlorobenzoxazole, 5methylbenzoxazole, 5-phenylbenzoxazole, 6-methylbenzoxazole, 5,6-dimethylbenzoxazole, 4,6-dimethylbenzoxazole, 5-methoxybenzoxazole, 5-ethoxybenzoxazole, 6-chlorobenzoxazole, 6-methoxybenzoxazole, 5-hydroxybenzoxazole, 6-hydroxybenzoxazole, etc.); a naphthoxazole nucleus (e.g., α-naphthoxazole, β-naphthoxazole, etc.); a selenazole nucleus (e.g., 4-methylselenazole, 4-phenylselenazole, etc.); a benzoselenazole nucleus (e.g., benzoselenazole, 5-chlorobenzoselenazole, 5-methoxybenzoselenazole, 5-hydroxybenzoselenazole, tetrahydrobenzoselenazole, etc.); a naphthoselenazole nucleus (e.g., α-naphthoselenazole, β-naphthoselenazole, etc.); a thiazoline nucleus (e.g., thiazoline, 4-methylthiazoline, etc.); a 2-quinoline nucleus (e.g., quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 6-hydroxyquinoline, 8-hydroxyquinoline, etc.); a 4-quinoline nucleus (e.g., quinoline, 6-methoxyquinoline, 7-methylquinoline, 8-methylquinoline, etc.); a 1-isoquinoline nucleus (e.g., isoquinoline, 3,4-dihydroisoquinoline, etc.); a 3-isoquinoline nucleus (e.g., isoquinoline, etc.); a 3,3-dialkylindolenine nucleus (e.g., 3,3-dimethylindolenine, 3,3,5-trimethylindolenine, 3,3,7-trimethylindolenine, etc.), a 2-pyridine nucleus (e.g., pyridine, 3-methylpyridine, 4-methylpyridine, 5-methylpyridine, 3,4-dimethylpyridine, 4-chloropyridine, 3-hydroxypyridine, 3-phenylpyridine, etc.); a 4-pyridine nucleus (e.g., 2-methylpyridine, 3-methylpyridine, 3-chloropyridine, 2,6-dimethylpyridine, 3-hydroxypyridine, etc.); a 1-alkylimidazole nucleus (e.g., 1-methylimidazole, 1-ethyl-4-phenylimidazole, 1-butyl-4,5-dimethylimidazole, etc.); a 1-alkylbenzimidazole nucleus (e.g., 1-methylbenzimidazole, 1-butyl-4-methylbenzimidazole, 1-ethyl-5,6,-dichlorobenzimidazole, etc.); and, a 1-alkylnaphthimidazole nucleus (e.g., 1-ethyl-α-naphthimidazole, 1-methyl-β-naphthimidazole etc.); and, Q represents the nonmetallic atoms required to complete a alicyclic nucleus such as, for example, indanedione, cyclopentane, cyclohexane, etc. or a 5 to 6 membered heterocyclic nucleus, typically containing a hetero atom selected from nitrogen, sulfur, selenium, and oxygen, such as a 2-pyrazolin-5-one nucleus (e.g., 3-methyl-1-phenyl-2-pyrazolin-5-one, 1-phenyl-2-pyrazolin-5-one, 1-(2-benzothiazolyl)-3-methyl-2-pyrazolin-5-one, etc.); an isoxazolone nucleus (e.g., 3-phenyl-5-(4H)-isoxazolone, 3-methyl-5-(4H)-isoxazolone, etc.); an oxindole nucleus (e.g., 1-alkyl-2,3-dihydro-2-oxindoles, etc.), a 2,4,6-triketohexahydropyrimidine nucleus (e.g., barbituric acid or 2-thiobarbituric acid as well as their 1-alkyl (e.g., 1-methyl, 1-ethyl, 1-propyl, 1-heptyl, etc.) or 1,3-dialkyl (e.g., 1,3-dimethyl, 1,3-diethyl, 1,3-dipropyl, 1,3-diisopropyl, 1,3-dicyclohexyl, 1,3-di(β-methoxyethyl), etc., or 1,3-diaryl (e.g., 1,3-diphenyl, 1,3-di(p-chlorophenyl), 1,3-di(p-ethoxycarbonylphenyl), etc.), or 1-aryl (e.g., 1-phenyl, 1-p-chlorophenyl, 1-p-ethoxycarbonylphenyl), etc.) or 1-alkyl-3-aryl (e.g., 1-ethyl-3-phenyl, 1-n-heptyl-3-phenyl, etc.) derivatives); a rhodanine nucleus (i.e., 2-thio-2,4-thiazolidinedione series (such as rhodanine, 3-alkylrhodanines (e.g., 3-ethylrhodanine, 3-allylrhodanine, etc.), 3-carboxyalkylrhodanines (e.g., 3-(2-carboxyethyl)rhodanine, 3-(4-carboxybutyl)rhodanine, etc.), 3-sulfoalkylrhodanines (e.g., 3-(2-sulfoethyl)rhodanine, 3-(3-sulfopropyl)rhodanine, 3-(4-sulfobutyl)-rhodanine, etc.), or 3-arylrhodanines (e.g., 3-phenylrhodanine, etc.), etc.; a 2(3H)imidazo[1,2-a]pyridone nucleus; a 5,7-dioxo-6,7-dihydro-5-thiazolo[3,2-a]pyrimidine nucleus (e.g., 5,7-dioxo-3-phenyl-6,7-dihydro-5-thiazole[3,2-a]pyrimidine, etc.); a 2-thio-2,4-oxazolidinedione nucleus (i.e., those of the 2-thio-2,4(3H,5H)-oxazoledione series) (e.g., 3-ethyl-2-thio-2,4-oxazolidinedione, 3-(2-sulfoethyl)-2-thio-2,4-oxazolidinedione, 3-(4-sulfobutyl)-2-thio-2-thio-2,4-oxazolidine, 3-(3-carboxypropyl)-2-thio-2,4-oxazolidinedione, etc.); a thianaphthenone nucleus (e.g., 3-(2H)-thianaphthenone, etc.); a 2-thio-2,5-thiazolidinedione nucleus (i.e., the 2-thio-2,5-(3H,4H)-thiazolidinedione series) (e.g., 3-ethyl-2-thio-2,5-thiazolidinedione, etc.); a 2,4-thiazolidinedione nucleus (e.g., 2,4-thiazolidinedione, 3-ethyl-2,4-thiazolidinedione, 3-phenyl-2,4-thiazolidinedione, 3-α-naphthyl-2,4-thiazolidinedione, etc.); a thiazolidinone nucleus (e.g., 4-thiazolidinone, 3-ethyl-4-thiazolidinone, 3-phenyl-4-thiazolidinone, 3-α-naphthyl-4-thiazolidinone, etc.); a 2-thiazolin-4-one series (e.g., 2-ethylmercapto-2-thiazolin-4-one, 2-alkylphenylamino2-thiazolin-4-one, 2-diphenylamino-2-thiazolin-4-one, etc.); a 2-imino-4-oxazolidinone (i.e., pseudohydantoin) nucleus; a 2,4-imidazolidinedione (hydantoin) series (e.g.., 2,4-imidazolidinedione, 3-ethyl-2,4-imidazolidinedione, 3-phenyl-2,4-imidazolidinedione, 3-α-naphthyl-2,4-imidazolidinedione, 1,3-diethyl-2,4-imidazolidinedione, 1-ethyl-3-phenyl-2,4-imidazolidinedione, 1-ethyl-3-α-naphthyl-2,4-imidazolidinedione, 1,3-diphenyl-2,4-imidazolidinedione, etc.); a 2-thio-2,4-imidazolidinedione (i.e., 2-thiohydantoin) nucleus (e.g., 2-thio-2,4-imidazolidinedione, 3-ethyl-2-thio-2,4-imidazolidinedione, 3-(4-sulfobutyl)-2-thio-2,4-imidazolidinedione, 3-(2-carboxyethyl)-2-thio-2,4-imidazolidinedione, 3-phenyl-2-thio-2,4-imidazolidinedione, 3-α-naphthyl-2-thio-2,4-imidazolidinedione, 1,3-diethyl-2-thio-2,4-imidazolidinedione, 1-ethyl-3-phenyl-2-thio-2,4-imidazolidinedione, 1-ethyl-3-α-naphthyl-2-thio-2,4-imidazolidinedione, 1,3-diphenyl-2-thio-2,4-imidazolidinedione, etc.); a 2-imidazolin-5-one nucleus (e.g., 2-propylmercapto-2-imidazolin-5-one, etc.), etc. (especially useful are nuclei wherein Q represents a heterocyclic nucleus containing 5 atoms in the heterocyclic ring, 3 of said atoms being carbon atoms, 1 of said atoms being a nitrogen atom, and 1 of said atoms being selected from the group consisting of a nitrogen atom, an oxygen atom, and a sulfur atom).

Many of the above defined dye compounds containing desensitizing nuclei are powerful desensitizers for lightsensitive photographic silver halide emulsions and may be used when desensitization by means of dyes is required. The dyes absorb strongly and sharply, and their colors are uniform and deep. A number of them are bleachable dyes in filter layers or backing layers in photographic elements. The dye compounds can also be used as biological stains. Many of the above defined dye compounds without desensitizing nuclei are excellent sensitizers for negative silver halide emulsions.

Combinations of these novel dyes with themselves and with other sensitizing dyes may, of course, be used.

In accordance with the invention, we prepare the dye compounds defined by the above Formulas I, II and III from 1H-imidazo[4,5-b]pyrazine nucleus salt intermediates represented by the formula:

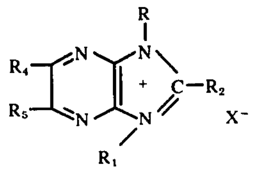

IV.

wherein R, $R_1$, $R_4$, $R_5$ and $X^-$ are as previously defined and $R_2$ represents a member selected from an alkyl group of from 1 to 4 carbon atoms, e.g., methyl, ethyl, propyl, butyl, secbutyl, etc. In general, our dyes are produced by heating a mixture of quaternary salt of above Formula IV with the appropriate intermediate. The reaction mixtures are advantageously heated in any of the suitable solvents used in dye snythesis including solvents such as ethanol, propanol, dioxane, pyridine, quinoline, and the like, at temperatures up to the reflux temperature of the mixture. Advantageously, the reaction is carried out in the presence of a basic condensing agent such as pyridine or other amines, e.g., trimethylamine, triethylamine, tri-n-propylamine, tri-n-butylamine, N-methylpiperidine, N-ethylpiperidine, N,N-dimethylaniline, N,N-diethylaniline, etc.

The symmetrical cyanine dyes of Formula I are prepared to advantage by heating a mixture of a compound of Formula IV (in which $R_2$ is methyl) with diethoxymethyl acetate (forms carbocyanine), trimethoxypropene (forms dicarbocyanine), 1-anilino-5-phenylimino-1,3-pentadiene hydrochloride (forms tricarbocyanine), etc., preferably in a solvent and in the presence of a basic condensing agent such as mentioned above.

The unsymmetrical cyanine dyes of Formula II are prepared advantageously by heating a mixture of a compound of Formula IV with a compound of the formula:

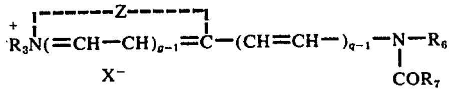

V.

wherein $R_3$, X and Z are as previously defined, *g* and *q* each represents a positive integer of from 1 to 2, $R_6$ represents an aryl group of from 6 to 20 carbon atoms, e.g., phenyl, naphthyl, etc., and $R_7$ represents an alkyl group of from 1 to 12 carbon atoms. This preferably carried out in a suitable solvent and in the presence of a basic condensing agent.

Our merocyanine dyes of Formula III are made to advantage by heating a mixture of compound of Formula IV (in which $R_2$ is methyl) with a compound of the formula:

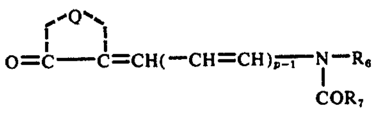

VI.

wherein Q is as defined previously and p represents a positive integer of from 1 to 2 and $R_6$ and $R_7$ are as previously defined.

The following examples will serve to illustrate more fully the manner whereby we prepare the dyes and show their utility in photographic emulsions. Temperatures are given as degrees centigrade in each of the examples.

EXAMPLE 1

1,1',3,3',5,5',6,6'-Octaphenyl-1H-imidazo[4,5-b]pyrazinocarbocyanine perchlorate

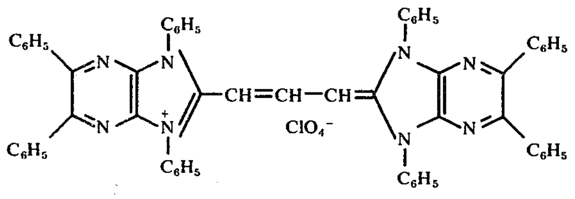

A mixture of 2-methyl-1,3,5,6-tetraphenyl-1H-imidazo[4,5-b]pyrazinium p-toluenesulfonate (2.44 g, 0.004 mole) and diethoxymethyl acetate (2.59 g, 0.016 mole) is heated with stirring in pyridine (15 ml) at reflux for 1.5 minutes. The mixture is then chilled and diluted to 350 ml by the slow addition of ether. The solid is collected by filtration, dissolved in hot methanol (200 ml) and treated with a hot aqueous solution of excess sodium perchlorate. The yield of dye after filtration is 2.1 g. (71%). The yield after two recrystallizations from methanol is 0.3 g (15%), m.p. > 300° C.

EXAMPLE 2

1,1',3,3'-Tetrakis(4-cyanophenyl)-5,5',6,6'-tetraphenyl-1H-imidazo[4,5-b]pyrazinocarbocyanine perchlorate

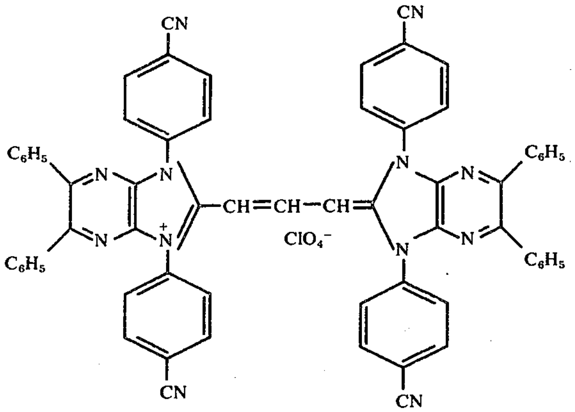

1,3-bis(4-cyanophenyl)-2-methyl-5,6-diphenyl-1H-imiazo[4,5-b]pyrazinium p-toluenesulfonate (1.32 g, 0.002 mole) is slurried in pyridine and diethoxymethyl acetate (1.30 g, 0.008 mole) is added. The mixture is heated with stirring at reflux for 2 minutes, then cooled. Ether (400 ml) is added slowly causing a blue oil to separate. The ether is decanted from the oil and methanol (300 ml) is added. The solution is filtered and the filtrate is treated with a concentrated solution of sodium perchlorate (excess). The slurry is chilled and filtered to collect the solid dye. Yield 0.19 g (17%).

The dye is dissolved in hot acetonitrile (10 ml), and the solution is diluted while hot with ethyl alcohol. It is then chilled. The yield of purified dye is 0.10 g (9%), m.p. > 310° C.

EXAMPLE 3

1,1',3,3'-Tetrakis(4-methoxyphenyl)-5,5',6,6'-tetraphenyl-1H-imiazo[4,5-b]pyrazinocarbocyanine perchlorate

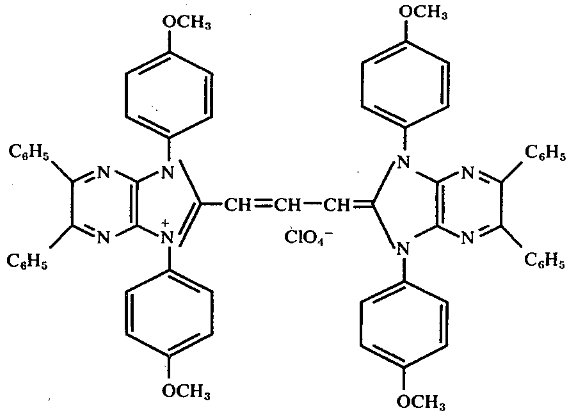

1,3-bis(4-methoxyphenyl)-2-methyl-5,6-diphenyl-1H-imiazo[4,5-b]pyrazinium p-toluenesulfonate (2.71 g, 0.004 mole) is moistened with enough pyridine to make a thick slurry, to which diethoxymethyl acetate (2.59 g, 0.016 mole) is added. The mixture is heated at reflux for 2 minutes, then chilled. Ether is added to separate the dye as a blue oil. The ether is decanted and the oil is dissolved in hot methanol. The solution is treated with a warm aqueous solution of sodium perchlorate (excess). After cooling, the solid is filtered off, stirred in 500 ml hot ethyl alcohol, filtered again and the filtrate chilled. The solid dye is filtered off and then dried. Yield 1.33 g (60%). The dye is recrystallized again from 400 ml ethyl alcohol plus 4 ml triethylamine. After still another recrystallization from methanol, the yield of pure dye is 0.10 g (4.5%), m.p. 354°-355° C (dec.). EXAMPLE 4 1,1',3,3'-Tetraethyl-5,5',6,6'-tetraphenyl-1H-imidazo[4,5-b]pyrazinocarbocyanine perchlorate

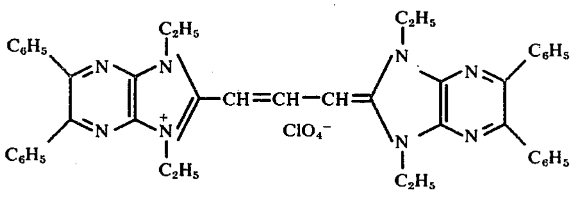

1,3-diethyl-2-methyl-5,6-diphenyl-1H-imidazo-[4,5-b]pyrazinium p-toluenesulfonate (2.06 g, 0.004 mole) is slurried in pyridine. Diethoxymethyl acetate (2.59 g, 0.016 mole) is added and the mixture is heated at reflux for 2 minutes, then chilled. Ether (500 ml) is added which causes the dye to separate as an oil. The ether is decanted and the oil taken up in methanol, treated with aqueous solution of sodium perchlorate and chilled. The solid is filtered off, suspended in 200 ml boiling ethyl alcohol and filtered hot. After chilling, the solid dye which precipitates is filtered off and dried. Yield 0.26 g. The dye is recrystallized again from ethyl alcohol plus 1.5 ml triethylamine. Yield 0.24 g (15%), m.p. 259°-260° C (dec.).

EXAMPLE 5

1,1',3,3'-Tetraethyl-5,5',6,6'-tetramethyl-1H-imidazo[4,5-b]pyrazinocarbocyanine perchlorate

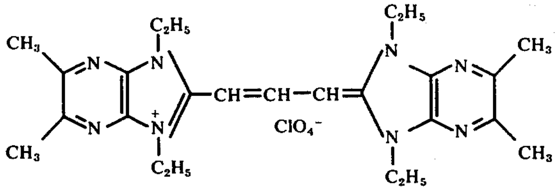

1,3-diethyl-2,5,6-trimethyl-1H-imidazo[4,5-b]-pyrazinium p-toluenesulfonate (1.00g, 0.0025 mole) is slurried in pyridine. Diethoxymethyl acetate (1.66 g, 0.0103 mole) is added and the mixture heated at reflux for 2 minutes, then cooled and diluted with ether (400 ml). The solid is filtered off and dissolved in hot tetrahydrofuran. The solution is filtered to remove insoluble colorless crystals and the filtrate is evaporated to dryness. The residue is dissolved in methanol, treated with an aqueous solution of sodium perchlorate (excess) and the solid dye which precipitates is filtered off and dried. Yield 0.13 g (19%), m.p. 272°–273° C (dec.).

EXAMPLE 6

1,1',3,3'-Tetramethyl-1H-imidazo[4,5-b]pyrazinocarbocyanine p-toluenesulfonate

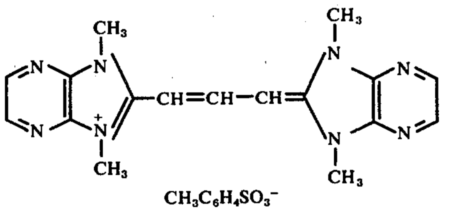

A mixture of 1,2,3-trimethyl-1H-imidazo[4,5-b]-pyrazinium p-toluenesulfonate (3.34 g, 0.01 mole) and diethoxymethyl acetate (4.86 g, 0.03 mole) is dissolved in dimethylformamide (10 ml) containing acetic anhydride (10 drops) and heated at gentle reflux for 3 minutes. The reaction mixture is chilled, diluted with ether (200 ml) and the solid which separates is filtered off and dried. The dye is recrystallized from ethyl alcohol. Yield 0.40 g (39%).

The following examples describe the preparation of unsymmetrical carbocyanines.

EXAMPLE 7

2-[2-(1-Methyl-2-phenyl-3-indolyl)vinyl]-1,3,5,6-tetraphenyl-1H-imidazo[4,5-b]pyrazinium bromide

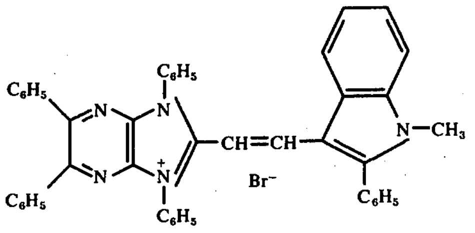

A mixture of 2-methyl-1,3,5,6-tetraphenyl-1H-imidazo[4,5-b]pyrazinium p-toluenesulfonate (1.53 g, 0.0025 mole) and 3-formyl-1-methyl-2-phenylindole (0.58 g, 0.0025 mole) are suspended in acetic anhydride and heated at reflux for 1.5 minutes, then chilled and diluted to 350 ml volume by the slow addition of ether. The solid which separates is filtered off, dissolved in methanol, treated with an aqueous methanol solution of sodium bromide (excess). The solid dye is filtered off and recrystallized from methanol (300 ml). Yield 0.56 g (30%). The dye is recrystallized again from methanol (60 ml). Yield 0.37 g (20%), m.p. >300°.

EXAMPLE 8

1,3-Bis(4-cyanophenyl)-2-[2-(1-methyl-2-phenyl-3-indolyl)vinyl]-5,6-diphenyl-1H-imidazo[4,5-b]-pyrazinium perchlorate

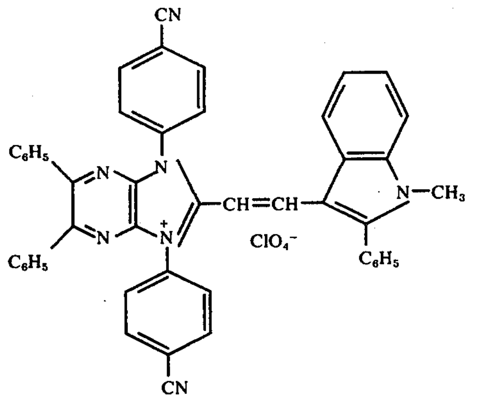

A mixture of 1,3-bis(4-cyanophenyl)-2-methyl-5,6-diphenyl-1H-imidazo[4,5-b]pyrazinium p-toluenesulfonate (1.00 g, 0.0015 mole) and 3-formyl-1-methyl-2-phenylindole (0.40 g, 0.0017 mole) is suspended in acetic anhydride (5ml) and heated at reflux for 4 minutes. After being chilled, diluted with p-dioxane (10 ml) and filtered to remove colorless solid, the filtrate is diluted to 200 ml with ether and the crude solid dye is filtered off and dried. The yield of crude dye is 0.75 g. The dye is dissolved in methanol and treated with an aqueous solution of sodium perchlorate (excess). The dye which precipitates is filtered off. Yield 0.29 g. It is purified once more by dissolving it in acetonitrile (10 ml) to which a trace of perchloric acid has been added, filtering the solution, and diluting the filtrate with ethyl alcohol (60 ml). A solution of sodium perchlorate (4 g) in methanol is added and the filtrate chilled. The solid dye is filtered off, washed with methanol and dried. The yield is 0.13 g (11%), m.p. >310° C.

EXAMPLE 9

1,3-Bis(4-methoxyphenyl)-2-[2-(1-methyl-2-phenyl-3-indolyl)vinyl]-5,6-diphenyl-1H-imidazo[4,5-b]pyrazinium perchlorate

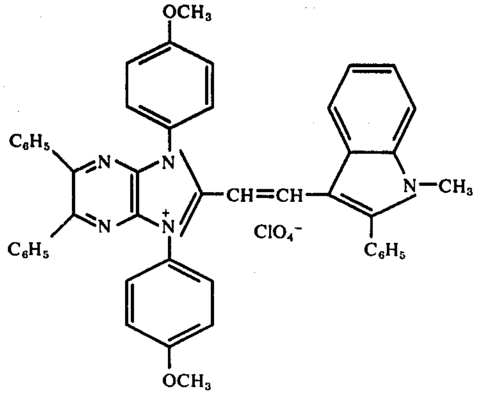

A mixture of 1,3-bis(4-methoxyphenyl)-2-methyl-5,6-diphenyl-1H-imidazo[4,5-b]pyrazinium p-toluenesulfonate (2.20 g, 0.0033 mole) and 3-formyl-1-methyl-2-phenylindole (0.77 g, 0.0033 mole) is suspended in acetic anhydride (13 ml) and heated at reflux for 2.5 minutes. After cooling, the mixture is diluted with ether (400 ml), the ether is decanted and the orange oil, which has separated, is dissolved in methanol, treated with sodium perchlorate (excess) in aqueous solution and chilled. The solid is filtered off and dried. Yield 2.07 g. It is suspended in 200 ml boiling ethyl alcohol containing 0.5 ml triethylamine and the suspension is chilled and filtered. Yield 1.31 g. This material is recrystallized from a tetrahydrofuran acetonitrile mixture. Yield 0.38 g (14%), m.p. 339°–341° C dec.

EXAMPLE 10

1,3-Diethyl-2-[2-(1-methyl-2-phenyl-3-indolyl)vinyl]-5,6-diphenyl-1H-imidazo[4,5-b]pyrazinium perchlorate

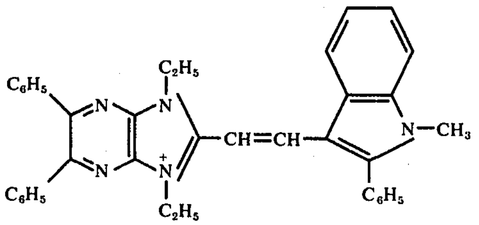

A mixture of 1,3-diethyl-2-methyl-5,6-diphenyl-1H-imidazo[4,5-b]pyrazinium p-toluenesulfonate (2.00 g, 0.0039 mole) and 3-formyl-1-methyl-2-phenylindole (0.91 g, 0.0039 mole) is suspended in acetic anhydride (11 ml) and heated at reflux for 2.5 minutes, then cooled. After diluting slowly to 400 ml volume with ether the semi-crystalline solid is filtered off, redissolved in methanol and treated with an aqueous solution of excess sodium perchlorate. The solid which separates is filtered off, washed with methanol and dried. The solid is suspended in ethyl alcohol (15 ml) to which 0.3 ml triethylamine has been added. This is heated to boiling, cooled, and filtered. The solid is washed with ethyl alcohol and dried. Yield 1.61 g. This material is recrystallized three more times from ethyl alcohol. The yield of pure dye is 0.33 g (13%), m.p. 265°–267° C dec. (melted at 173° then resolidified).

EXAMPLE 11

1,3-Diethyl-5,6-dimethyl-2-[2-(1-methyl-2-phenyl-3-indolyl)vinyl]-1H-imidazo[4,5-b]pyrazinium perchlorate

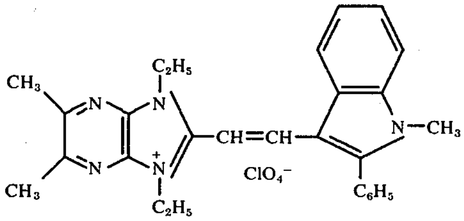

A mixture of 1,3-diethyl-2,5,6-trimethyl-1H-imidazo-[4,5-b]pyrazinium p-toluenesulfonate (0.51 g, 0.0013 mole) and 3-formyl-1-methyl-2-phenylindole (0.32 g, 0.0013 mole) is suspended in 10 ml acetic anhydride and the mixture is heated, with stirring, to reflux for 75 minutes. After cooling, it is diluted with ether to a 200 ml volume and chilled overnight. The ether is decanted and the oil left behind is dissolved in methanol and treated with an aqueous solution of sodium perchlorate (excess). Water is added until precipitation begins. The solid is filtered off, washed with water and methanol and dried. Yield 0.21 g. This material is recrystallized from an acetonitrile-ethyl alcohol mixture. Yield 0.18 g (26%), m.p. 272°–274° C dec.

EXAMPLE 12

3'-Ethyl-1,3,5,5',6-pentaphenyl-1H-imidazo[4,5-b]-pyrazinooxacarbocyanine p-toluenesulfonate

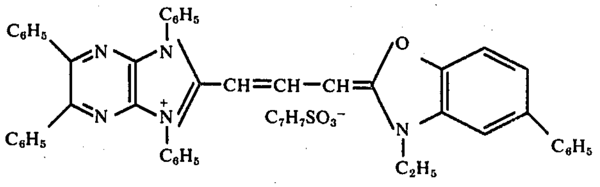

2-methyl-1,3,5,6-tetraphenyl-1H-imidazo[4,5-b]pyrazinium p-toluenesulfonate (2.00 g, 0.0033 mole) is added to a solution of 2-(2-anilinovinyl)-3-ethyl-5-phenylbenzoxazolium iodide (1.53 g, 0.0033 mole) in a mixture of acetic anhydride (5 ml) and acetonitrile (5 ml), which has been heated to reflux then cooled to room temperature. Triethylamine (1.2 g) is added and a spontaneous exothermic dye forming reaction occurs which is allowed to proceed for 10 minutes. After chilling, the solid dye is filtered off, washed with acetonitrile and dried. A yield of 2.20 g of dye iodide is obtained. This material is suspended in methanol (25 ml), p-toluenesulfonic acid (1.00 g) and propylene oxide (1.00 g) are added and the mixture is refluxed for 22 hours. It is stirred at room temperature for another 36 hours. The solid is filtered off, washed with methanol and dried. Yield 1.19 g (53%), m.p. 295°–296° C dec.

EXAMPLE 13

3'-Ethyl-1,3-bis(4-methoxyphenyl)-5,5',6-tri-phenyl-1H-imidazo[4,5-b]pyrazinooxacarbocyanine p-toluenesulfonate

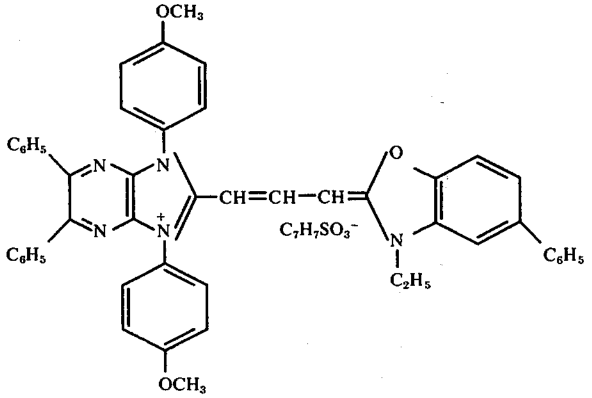

1,3-bis(4-methoxyphenyl-2-methyl-5,6-diphenyl-1H-imidazo[4,5-b]pyrazinium p-toluenesulfonate (2.22 g, 0.003 mole) is added to a solution of 2-(2-anilinovinyl)-3-ethyl-5-phenylbenzoxazolium iodide in a solvent mixture of acetic anhydride (5 ml) and acetonitrile (5 ml) which has been heated to reflux then cooled to room temperature. Tri-ethylamine (1.16 g) is added and the resulting exothermic dye forming reaction is allowed to proceed for 10 minutes, warmed briefly and chilled. The solid dye is filtered off, washed with acetonitrile and dried. The yield of dye is 2.37 g. This material is suspended in methanol (25 ml) and then p-toluenesulfonic acid (1.5 g) and propylene oxide (1.5 g) are added. The mixture is refluxed 17 hours, chilled, filtered and the solid dye is dried. It is recrystallized from, 1,4-dioxane (50 ml). Yield 0.17 g (7%), m.p. 258°–259° C dec.

EXAMPLE 14

1,3,3'-Triethyl-5,5',6-triphenyl-1H-imidazo[4,5-b]pyrazinooxacarbocyanine chloride

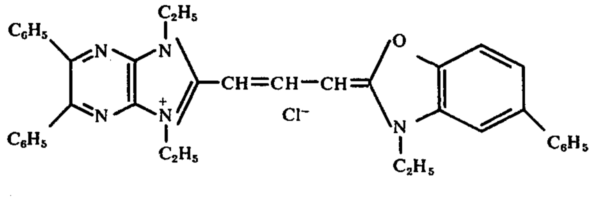

1,3-diethyl-2-methyl-5,6-diphenyl-1H-imidazo[4,5-b]pyrazinium p-toluenesulfonate (2.00 g, 0.0039 mole) is added to a solution of 2-(2-anilinovinyl)-3-ethyl-5-phenylbenzoxazolium iodide (1.82 g, 0.0039 mole) in a solvent mixture of acetic anhydride (5 ml) and acetonitrile (7 ml) which has been heated to boiling and then cooled. Triethylamine (1.4 g) is added and the resulting exothermic dye forming reaction is allowed to proceed for 10 minutes, warmed briefly and then chilled. The solid dye is filtered off, washed with acetonitrile and dried. A yield of 2.61 g of dye is obtained. A 0.25 g portion of the dye iodide is dissolved in methanol and treated with an aqueous solution of sodium perchlorate (excess) and chilled. The solid dye is filtered off and dried. Yield 0.21 g of dye perchlorate. This material is suspended in methanol (50 ml) and Amberlite IRA-400 anion exchange resin, $Cl^-$, is added and the mixture is stirred and warmed for 3 hours. The resin is filtered off, washed with methanol and the filtrate concentrated to dryness. The residue is dissolved in 50% aqueous ethyl alcohol, heated to boiling and cooled. After filtration the filtrate is concentrated to a small volume and more water is added. The solid dye is filtered off and dried. Yield 0.10 g (40% overall yield based on theoretical iodide to chloride conversion), m.p. 262°–263° C dec.

EXAMPLE 15

1,3,3'-Triethyl-5,6-dimethyl-1H-imidazo[4,5-b]-pyrazinooxacarbocyanine perchlorate

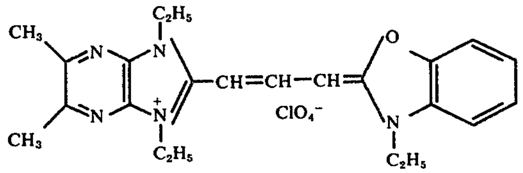

A mixture of 1,3-diethyl-2,5,6-trimetyl-1H-imidazo[4,5-b]pyrazinium p-toluenesulfonate (1.50 g, 0.0038 mole) and 2-(2-acetanilidovinyl)-3-ethylbenzoxazolium iodide (1.67 g, 0.0038 mole) is suspended in acetonitrile and triethylamine (0.8 g) is then added. The mixture is warmed to 70° then chilled and filtered. The solid dye is washed with acetonitrile and dried. The yield is 1.75 g. A 0.9 g portion is dissolved in methanol, treated with an aqueous solution of sodium perchlorate and the solid dye perchlorate filtered off, washed with methanol and dried. Yield 0.87 g. The dye is recrystallized from acetonitrile (25 ml) washed with ethyl alcohol and dried. Yield 0.71 g, (70% based on theoretical iodide to perchlorate conversion), m.p. 283°–284°.

EXAMPLE 16

3′-Ethyl-1,3-dimethyl-1H-imidazo[4,5-b]pyrazinooxacarbocyanine iodide

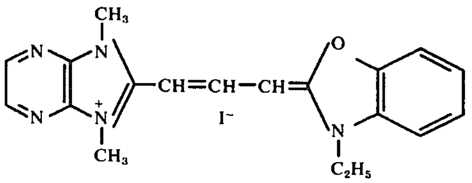

A mixture of 1,2,3-trimethyl-1H-imidazo[4,5-b]pyrazinium p-toluenesulfonate (0.63 g, 0.0019 mole) and 2-(2-acetanilidovinyl)-3-ethylbenzoxazolium iodide (0.82 g, 0.0019 mole) is suspended in acetonitrile (100 ml). Ethyl diisopropylamine (0.25 g) is added and the reaction mixture is refluxed 15 minutes and then cooled. The solution is poured into ether and stirred. The precipitate is filtered off, stirred in hot water and cooled, filtered again to obtain 0.87 g crude dye. After two recrystallizations from methanol, the yield of dye is 0.12 g (14%), m.p. 274°–275° C.

EXAMPLE 17

1,3,3′-Triethyl-5,6-dimethyl-4′,5′-benzo-1H-imidazo[4,5-b]pyrazinothiacarbocyanine perchlorate

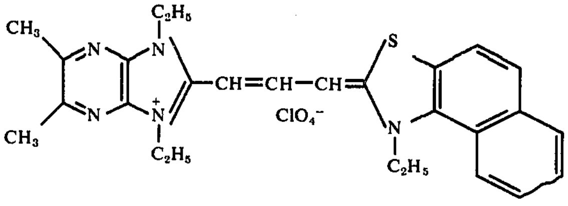

1,3-diethyl-2,5,6-trimethyl-1H-imidazo[4,5-b]pyrazinium p-toluenesulfonate (1.50 g, 0.0038 mole) is added to a solution of 2-(2-anilinovinyl)1-ethylnaphtho[1,2-d]thiazolium p-toluenesulfonate (1.93 g, 0.0038 mole) in a solvent mixture of acetic anhydride (5 ml) and acetonitrile (5 ml) which has been heated to boiling and then cooled. An immediate, exothermic dye forming reaction occurs when triethylamine is added. The reaction is heated to 70°–80° briefly and then chilled. The dye is filtered off, washed with tetrahydrofuran and dried. The yield of crude dye is 2.41 g (92%). The yield of dye after recrystallization from acetonitrile (100 ml/g) is 54%, m.p. 295°–296° C dec.

EXAMPLE 18

3′-Ethyl-1,3-dimethyl-4′,5′-benzo-1H-imidazo[4,5-b]pyrazinothiacarbocyanine iodine

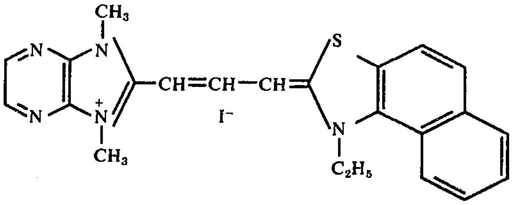

A mixture of 1,2,3-trimethyl-1H-imidazo[4,5-b]pyrazinium p-toluenesulfonate (0.40 g, 0.0012 mole) and trietylamine (0.17 ml) is added to a suspension of 2-(2-anilinovinyl)-1-ethylnaphtho[1,2-d]thiazolium p-toluenesulfonate (0.60 g, 0.0012 mole) and acetic anhydride (0.12 g) in pyridine (100 ml), the suspension having been first heated briefly. The reaction mixture is refluxed 15 minutes then poured into an aqueous sodium iodide solution (14.6 g/800 ml $H_2O$). The dye is filtered off, washed with water and methanol and then dried. Yield 0.43 g. After two recrystallizations from ethyl alcohol the yield is 0.14 g (22%), m.p. 275°–276° C.

EXAMPLE 19

5,6-Dichloro-1,3-diethyl-1′,3′,5′,6′-tetraphenylbenzimidazolo-1H-imidazo[4,5-b]pyrazinocarbocyanine perchlorate

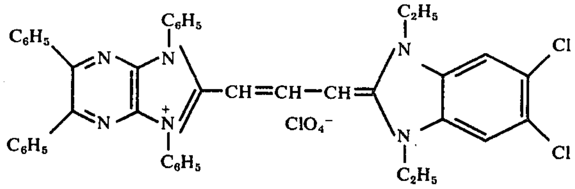

2-methyl-1,3,5,6-tetraphenyl-1H-imidazo[4,5-b]pyrazinium p-toluenesulfonate (2.00 g, 0.0033 mole) 5,6-dichloro-1,3-diethyl-2-[(N-phenyl-p-toluenesulfonamido)]vinyl benzimidazolium iodide (2.11 g, 0.0033 mole) and ethyldiisopropyl amine (0.85 g) are added to pyridine (15 ml) and the mixture heated at reflux for 12 minutes. After cooling, the reaction mixture is filtered to remove some nearly colorless crystals and then diluted with ether (100 ml). The solid which precipitates is filtered off and extracted with hot tetrahydrofuran. The extracts are filtered and the filtrate evaporated to dryness. The residue is dissolved in methanol and treated with an aqueous solution of sodium perchlorate (5 g). The perchlorate which precipitates is filtered off and recrystallized twice from methanol. Yield 0.10 g(4%), m.p. 296°–297° dec.

EXAMPLE 20

1,3-Dimethyl-2-[2-(1-phenyl-3-indazolyl)vinyl]1H-imidazo[4,5-b]pyrazinium p-toluenesulfonate

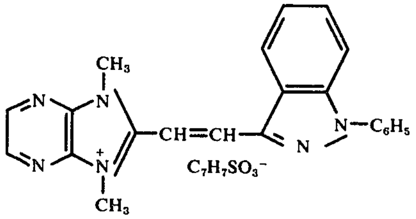

A mixture of 1,2,3-trimethyl-1H-imidazo[4,5-b]pyrazinium p-toluenesulfonate (1.67 g, 0.050 mole) and 3-formyl-1-phenylindazole (1.11 g, 0.050 mole) is heated together in acetic anhydride (15 ml) at reflux for 30 minutes. After chilling, ether (500 ml) is added and the solid which separates is filtered off and dried. Yield 1.92 g, (72%). After recrystallization from water the yield of dye is 0.55 g (41%).

EXAMPLE 21

1',3'-Dimetyl-1,3,5,6-tetraphenyl-1H-imidazo[4,5-b]pyrazino-1H-imidazo[4,5-b]quinoxalinocyanine perchlorate

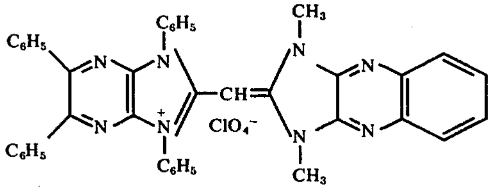

A mixture of 2-methyl-1,3,5,6-tetraphenyl-1H-imidazo[4,5-b]pyrazinium p-toluenesulfonate (1.83 g, 0.003 mole) and 2-hydroxyiminomethyl-1,3-dimethyl-1H-imidazo[4,5b]quinoxalinium perchlorate (0.95 g, 0.003 mole) is heated in acetic anhydride (15 ml) with triethylamine (0.03 g, 0.003 mole) at reflux for 2 minutes and then chilled. Ether (150 ml) is added and the solid which separates is filtered off, washed with ether and dried. Yield 1.2 g (55%). After two recrystallizations from acetic acid the yield is 0.7 g (32%). The solid is suspended in refluxing benzene (200 ml.) and filtered while not. Yield 0.6 g (27%), m.p. 254°–257° C dec.

EXAMPLE 22

3'-Ethyl-6'-nitro-1,3,5,6-tetraphenyl-1H-imidazo[4,5-b]pyrazinothiacarbocyanine bromide

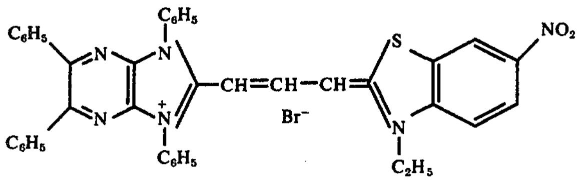

A mixture of 2-methyl-1,3,5,6-tetraphenyl-1H-imidazo[4,5-b]pyrazinium p-toluenesulfonate (1.53 g, 0.0025 mole) and 3-ethyl-2-formylmethylene-6-nitrobenzothiazoline (0.63 g, 0.0025 mole) is heated at reflux in acetic anhydride for 2 minutes and then chilled and diluted with ether (200 ml). The ether is decanted and the semi-solid residue is stirred with water (50 ml) and filtered. The yield of crude dye is 2.1 g. The crude dye is dissolved in hot methanol (75 ml) and the solution treated with an aqueous solution of excess sodium bromide. The dye is precipitated. It is filtered off, washed with methanol and dried. Yield 1.3 g (69%). The dye is recrystallized from methanol (400 ml). Yield 0.8 g (43%), m.p. 241°–244° C dec.

EXAMPLE 23

1',3'-Diallyl-1,3,5,6-tetraphenyl-1H-imidazo[4,5-b]pyrazino-1H-imidazo[4,5b]quinoxalinocarbocyanine perchlorate

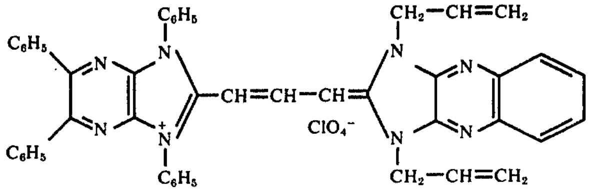

A mixture of 2-methyl-1,3,5,6-tetraphenyl-1H-imidazo[4,5-b]pyrazinium p-toluenesulfonate (1.41 g, 0.0023 mole) and 1,3-diallyl-2-formylmethylene-2,3-dihydro-1H-imidazo[4,5-b]quinoxaline (0.67 g, 0.0023 mole) is heated in acetic anhydride (15 ml) for 2 minutes and then chilled. Ether (400 ml) is added and the solid which separates is filtered, washed with ether and then dried. It is dissolved in hot methanol (150 ml) and treated with an aqueous solution of excess sodium perchlorate. The precipitated dye is filtered off and dried. Yield 1.5 g (80%). After two recrystallizations from methanol, the yield is 0.75 g (40%), m.p. 273° C dec.

The following example illustrates the preparation of a merocyanine dye containing an imidazo[4,5-b]pyrazine nucleus.

EXAMPLE 24

3-Ethyl-5-[2-(2,3-dihydro-1,3-dimethyl-1H-imidazo[4,5-b]pyrazolylidene ethylidene]rhodanine

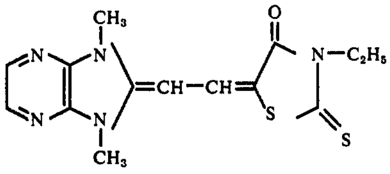

1,2,3-trimethyl-1H-imidazo[4,5-b]pyrazinium p-toluenesulfonate (0.37 g, 0.0012 mole), 5-acetanilidomethylene-3-ethylrhodanine (0.40 g, 0.0012 mole) and triethylamine (2.0 ml) are added in order to ethyl alcohol (100 ml) and the resulting mixture is refluxed for ten minutes. After chilling, the crude solid dye is filtered off and dried. Yield 0.22 g. The dye is purified by dissolving it in a small amount of pyridine and recrystalized by the addition of ethyl alochol. The yield after two such recrystallizations is 0.21 g (55%), m.p. 324°–325° C dec.

EXAMPLE 25

This example describes tests for acid-base sensitivity of the dyes of the invention. The sensitivity is determined in buffered solutions at pH 10.1 and at pH 2.4. The spectrophotometric analyses are conducted in yellow light and the dye solutions are stored in the dark between tests. Approximate spectral half lives, $t_{1/2}$, are given in Table 1. This example indicates that the dyes are useful as filter dyes since at high pH, such as those used in processing solutions, they could be decolorized.

Table 1

| Dye | t at pH 10.1 | t at pH 2.4 |
|---|---|---|
| Example 7 | 1 hour | stable |
| Example 14 | 8 days | stable |
| Example 3 | 2 weeks | stable |
| Example 13 | 4 days | 2 weeks |
| Example 4 | very slightly sensitive | stable |
| Example 2 | 1 hour | 2 weeks |
| Example 8 | 5 minutes | 5 days |

EXAMPLE 26

This example illustrates the use of the dyes of this invention as photobleachable image dyes.

The dye of Example 20 is dissolved in a chloroform solution of Geon 222 polymer (B.F. Goodrich product; contains cyano groups but no carbonyl groups) and this solution is coated on Estar film base at a thickness of 0.008 inch.

Two strips are exposed for 2½ minutes each to a General Electric Tungsten 500 watt photospot at a distance of 20 inches through WRIA filter (to remove UV radiation of wavelengths less than 400 nm) and a positive imaging transparency. Both strips have a good recognizable image which is very light yellow in exposed areas and dark yellow in unexposed areas.

Strip 1 is kept in the dark for 13 days at the end of which time the strip shows no apparent change in contrast. Strip 2 is left exposed to ordinary room illumination. The image gradually fades and completely disappears in 45 minutes. The strip is a uniform pale yellow with a green fluorescence.

EXAMPLE 27

The dyes in Table 2 are tested in a 0.2 μm sulfur- and gold-sensitized, cubic-grained gelatino-silver bromoiodide emulsion containing 2.5 mole percent iodide. The dyes are added to separate portions of the emulsion and the emulsion coated at 11 mg/dm$^2$ on a cellulose acetate support. A sample of each coating is exposed to a tungsten light source in an Eastman 1B Sensitometer through a wedge spectrograph and through a continuous step wedge, using a Wratten 16 filter (minus blue). The coatings are developed in a Kodak Versamat roller transport processor for 80 seconds at 23° C in an Elon-hydroquinone developer, fixed, washed and dried.

Control 1 — Undyed Emulsion

Control 2 — Emulsion with the dye 3-carboxymethyl5-[(3-methyl-2-thiazolidinylidene)-1-methylethylidene]-rhodanine.

Table 2

| Dye | Level × $10^{-4}$ moles/ mole Ag | Relative 365 Line Speed | Relative Minus Blue Speed | Fog | Sensitizing max (nm) | Sensitizing Range (nm) |
|---|---|---|---|---|---|---|
| Control 1 | — | 100 | — | .06 | | |
| Control 2 | 6.0 | 214 | 100 | .06 | 540 | |
| Example 5 | 6.0 | 229 | 631 | .35 | 600 | 500–625 |
| Example 15 | 6.0 | 269 | 363 | .32 | 555 | 480–590 |
| Example 17 | 6.0 | 246 | 631 | .33 | 610 | 500–650 |
| Example 11 | 6.0 | 78 | — | .06 | — | —* |
| | | | | | | *No Spectral Response |
| Control 1 | | 100 | — | .06 | | |
| Control 2 | | | 100 | .08 | 540 | |
| Example 14 | 6.0 | 246 | 151 | .09 | 570 | 480–610 |
| Example 13 | 6.0 | 141 | 48 | .08 | 565 | 490–610 |
| Example 3 | 6.0 | 105 | 7.6 | .20 | 640 | 600–660 |
| Example 4 | 6.0 | 289 | 331 | .30 | 610 | 500–660 |
| Example 2 | 6.0 | — | — | .23 | — | —* |
| | | | | | | *No Spectral Response |

EXAMPLE 28

The dyes in Table 3 are tested as those in Table 2 except that they are developed 8 minutes in Kodak Developer DK-50, fixed, washed and dried.

The controls are the same as for Table 2.

Table 3

| Dye | Level × $10^{-4}$ moles/ mole Ag | Relative 365 Line Speed | Relative Minus Blue Speed | Fog | Sensitizing max (nm) | Sensitizing Range (nm) |
|---|---|---|---|---|---|---|
| Control 1 | — | 100 | — | .04 | | |
| Control 2 | 6.0 | 269 | 100 | .04 | 540 | |
| Example 19 | 6.0 | 302 | 372 | .09 | 580 | 490–620 |
| Example 1 | 6.0 | 10.2 | — | .10 | — | —* |
| Example 12 | 6.0 | 282 | 186 | .07 | 570 | 500–620 |
| Example 9 | 6.0 | 58 | 7.8 | .06 | 545 | 500–580 |
| Example 10 | 8.0 | 50 | 3.5 | .07 | 515 | 490–560 |

*No Spectral Response

EXAMPLE 29

The following dye is tested as a reversal sensitizer in a fogged direct positive emulsion. The emulsion is a 0.2 μm cubic-grained gelatino-silver bromoiodide emulsion, which contains 2.5 mole percent iodide, and which is reduced and gold-fogged as in Example 3 of U.S. Pat. No. 3,501,307.

The dye is added to the emulsion at the concentration indicated and coated at 11.0 mg/dm$^2$ on a cellulose acetate support. A sample of the coating is exposed to a tungsten light source in an Eastman 1B Sensitometer through a wedge spectrograph with a continuous step wedge, using no filter.

The coating is developed for 8 minutes in Kodak DK-50 developer, fixed, washed and dried. Table 4 lists the results.

Table 4

| Dye | Level $\times 10^{-4}$ moles/ mole Ag | Relative 365 Line Speed | Relative Clear Speed | Fog | Sensitizing max (nm) | Sensitizing Range (nm) |
|---|---|---|---|---|---|---|
| Control 1 | — | 0.00 | — | 165 | — | — |
| Control 2 | 8.0 | 100 | 100 | 136 | 550 | 460–610 |
| Example 9 | 6.0 | 105 | 41 | 62 | 540 | 550–590 |

Control 1 — Undyed Emulsion (Average)
Control 2 — Emulsion plus 1,3-Diethyl-2-[2-(1-methyl-2-phenyl-3-indolyl) vinyl]-1H-imidazo[4,5-b]quinoxalinium iodide.

The examples which follow illustrate the preparation of a number of intermediate compounds.

EXAMPLE 30–35

The 2-methyl-1H-imidazo[4,5-]pyrazinium salts are prepared by reaction of a 1,2-bis(N-substituted amino) pyrazine of the formula

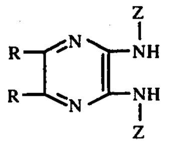

with acetic anhydride ($Ac_2O$) in the presence of p-toluenesulfonic acid hydrate ($PtSH \cdot H_2O$) with the R and Z substituents defined according to Table 5. Table 5 lists the reaction conditions and salts formed of the formula

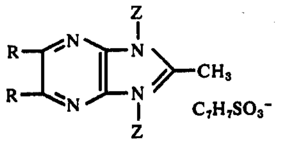

EXAMPLE 36

The 1,2-bis(N-substituted amino) pyrazine compounds are prepared according to the following reaction scheme:

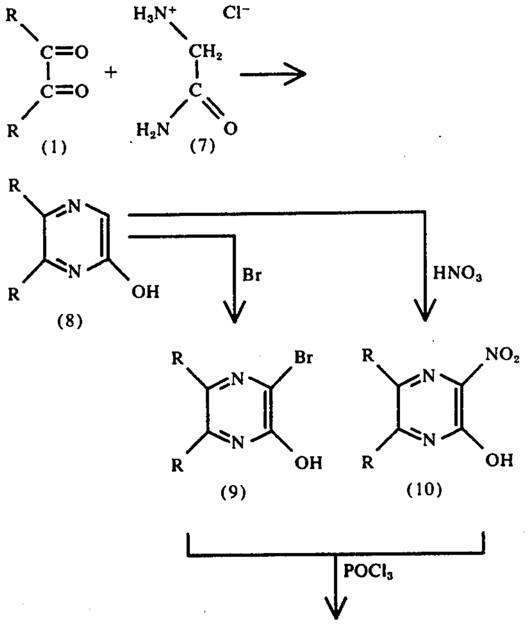

Table 5

| Example No. | Amount of Reactant | Amount of $AC_2O$ | Amount of $PtSH \cdot H_2O$ | R | Z | Reflux Time | Crude Yield | Recrystal. Solvent | Recrystal. Yield | mp |
|---|---|---|---|---|---|---|---|---|---|---|
| 30 | 11.0 g (0.027 m) | 50 ml | 8.0 g (excess) | $C_6H_5$ | $C_6H_5$ | 45 min. | 13.0 g (75%) | EtOH | 55% | 280–281° dec. |
| 31 | 2.26 g (0.0049 m) | 20 ml | 1.45 g (0.0073 m) | $C_6H_5$ | 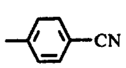 | few min. | 2.8 g (87%) | MeCN | 52% | 300–305°g dec. |
| 32 | 6.50 g (0.0137 m) | 30 ml | 4.08 g (0.02 m) | $C_6H_5$ | 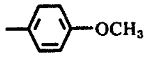 | 3 hr.* | 8.8 g (96%) | MeCN, ethyl alcohol | — | 293–294° dec. |
| 33 | 6.24 g (0.020 m) | 31 ml | 4.70 g (0.024 m) | $C_6H_5$ | $C_2H_5$ | 90 min. | 8.0 g (78%) | $Me_2CO$, MeCN | 22% | 217–219° dec. |
| 34 | 5.96 g (0.031 m) | 58 ml | 5.83 g (0.031 m)** | $CH_3$ | $C_2H_5$ | 5 ¼ hr.*** | 10.3 g (86%) | — | — | 167–169° dec. |
| 35 | 6.9 g (0.005 m) | 30 ml | 11 g (0.0055 m) | H | $CH_3$ | 30 min. | 13.4 g (80%) | i-PrOH | 60% | — |

*Product oiled out on addition of ether to the chilled reaction mixture. With the addition of tetrahydrofuran the product solidifies.
**Only 0.2 g of $PtSH \cdot H_2O$ is added initially. After 1 ¼ hr the remainder is added.
***Heating at 60° C product precipitates with addition of 30 ml tetrahydrofuran and 400 ml ether.

-continued

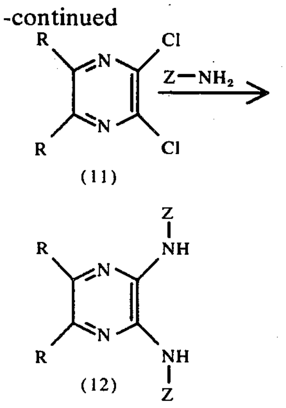

(11)

(12)

The 1,2-dichloropyrazines (11) are obtained either by bromination of (8) to yield (9), followed by treatment with phosphoryl chloride or by nitration of (8) to yield (10), followed by treatment with phosphoryl chloride. Treatment of (11 ) with primary amines yields the 1,2-bis)N-substituted amino) pyrazines (12) which are ring closed with acetic anhydride in the presence of strong acid to complete the synthesis of the desired quaternary salts as described in Examples 30–35.

The following examples illustrate the preparation of intermediates which can be used to prepare dyes of Formulas I, II and III wherein R and $R_1$ are different substituents. The methods of Examples 1, 12 and 24 can be employed to form the dyes.

EXAMPLE 37

2-Chloro-3-ethylamino-5,6-diphenylpyrazine

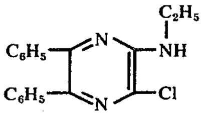

2,3-Dichloro-5,6-diphenylpyrazine (2.00 g, 0.0066 moles), is suspended in dimethylformamide (DMF) (12 ml) and treated with a solution of ethylamine (70% in water) (3.5 ml) in DMF (6 ml) and the mixture is warmed at 40°–45° C for 30 minutes then allowed to stand at room temperature for 6 hours. The solution is diluted with water (80 ml) and after standing overnight the solid is filtered off, washed with water and dissolved in hot ethyl alcohol, filtered, concentrated and cooled to yield 1.19 g of greenish-yellow solid. m.p. 115°–122°. This material is recrystallized from an ethyl alcohol-hexane mixture, yield 0.84 g, m.p. 121°–125°. Identity of the product is confirmed by infrared, nuclear magnetic resonance and mass spectra.

EXAMPLE 38

1-Ethyl-2-methyl-5,6-diphenyl-1H-imidazo[4,5-b]pyrazine

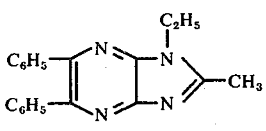

2-Chloro-3-ethylamino-5,6-diphenylpyrazine, (3.10 g, 0.01 moles) is dissolved in benzene (50 ml) and then triethylamine (1.29 g, 0.013 moles) and acetyl chloride (1.00 g, 0.013 moles) are added. The solution is refluxed 4½ hours, cooled to 15° C and filtrate. The filtrate is diluted with ethanol (3 ml), warmed briefly at 50° C and then all volatile materials evaporated. The resultant brown oil is treated with liquid ammonia (17 g) in ethanol (60 ml) in a bomb at 165° C for 12 hours. The solution is diluted with water (200 ml), cooled and the yellow precipitate filtered off. The solid is triturated with boiling 50% aqueous methanol, filtered, and the filtrate chilled. The product is collected by filtration. Yield 0.45 g (14%). It is recrystallized from benzene-heptane, m.p. 178.5°–180° C.

The identity of the product is confirmed by conversion of some of the product to the quaternary salt of Example 33 by treatment with ethyl p-toluenesulfonate. The alkylation by conventional methods with other alkylating agents such as propane sultone or chloroacetic acid yields the corresponding 3-sulfoalkyl or carboxymethyl analogs.

This invention has been described in detail with particular reference to certain preferred embodiments thereof, but it will be understood that variations and modifications can be effected within the spirit and scope of the invention.

We claim:

1. A silver halide sensitizing methine dye selected from those having one of the following formulas:

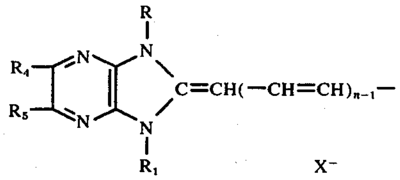

$X^-$

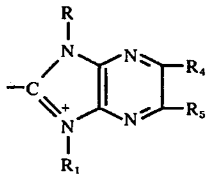

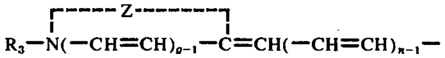

$X^-$

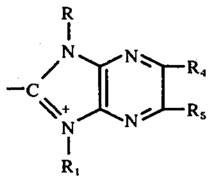

and

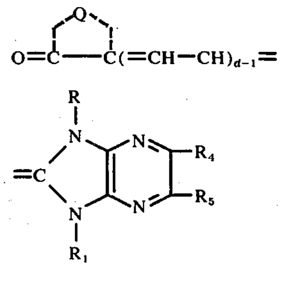

wherein $n$ represents a positive integer of from 1 to 4; $g$ represents a positive integer of from 1 to 2; $d$ represents a positive integer of from 1 to 3; R, $R_1$, $R_3$, $R_4$ and $R_5$ each represents a member selected from the group consisting of an alkyl, alkenyl, alkaryl and an aryl substituent; $R_4$ and $R_5$ also each represent in the alternative a member selected from the group consisting of alkoxy, halogen and cyano substituents, said substitutents R, $R_1$, $R_3$, $R_4$ and $R_5$ chosen such that the resulting nucleus is of the silver halide sensitizing type; $X^-$ represents an acid anion; Z represents the non-metallic atoms required to complete a sensitizing heterocyclic nucleus of the type used in cyanine dyes containing from 5 to 6 atoms in the heterocyclic ring; and Q represents the nonmetallic atoms required to complete a 5 or 6 membered silver halide sensitizing heterocyclic nucleus of the type used in merocyanine dyes.

2. A silver halide sensitizing methine dye of the formula

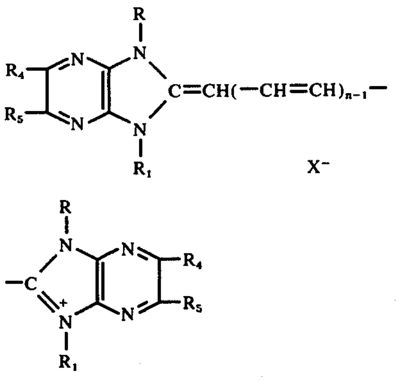

wherein $n$ represents a positive integer of from 1 to 4; R, $R_1$, $R_4$ and $R_5$ each represent a member independently selected from the group consisting of an alkyl group of 1 to 12 carbon atoms, an alkenyl group of 2 to 4 carbon atoms, an alkaryl substituent of 7 to 12 carbon atoms and an aryl group of 6 to 20 carbon atoms said substitutents R, $R_1$, $R_4$ and $R_5$ chosen such that the resulting nucleus is of the silver halide sensitizing type; and $X^-$ represents an acid anion.

3. A silver halide sensitizing machine dye of the formula

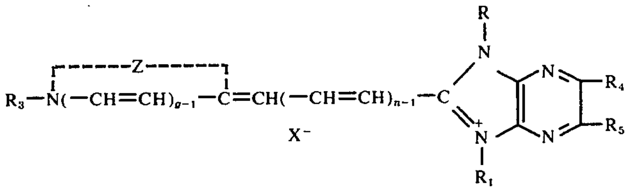

wherein $n$ represents a positive integer of from 1 to 4; g represents a positive integer of from 1 to 2; R, $R_1$, $R_4$ and $R_5$ each represent a member independently selected from a group consisting of an alkyl group of 1 to 12 carbon atoms; an alkenyl group of 2 to 4 carbon atoms, an alkaryl substitutent of 7 to 12 carbon atoms and an aryl group of 6 to 20 carbon atoms; $R_3$ represents an alkyl group of 1 to 12 carbon atoms said substitutents R, $R_1$, $R_3$, $R_4$ and $R_5$ chosen such that the resulting nucleus is of the silver halide sensitizing type; $X^-$ represents an acid anion; and Z represents the non-metallic atoms required to complete a silver halide sensitizing heterocyclic nucleus of the type used in cyanine dyes containing from 5 to 6 atoms in the heterocyclic ring and which in the alternative includes, in addition to the hetero nitrogen atom, a second hetero atom such as oxygen, sulfur, selenium or a second nitrogen atom.

4. A silver halide sensitizing methine dye of the formula

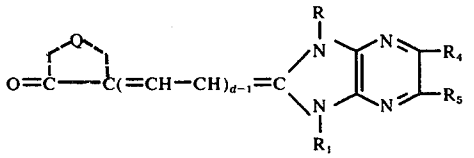

wherein $d$ represents a positive integer of from 1 to 3; R, $R_1$, $R_4$ and $R_5$ each represent a member independently selected from an alkyl group of 1 to 12 carbon atoms, an alkenyl group of 2 to 4 carbon atoms, an alkaryl substituent of 7 to 12 carbon atoms and an aryl group of 6 to 20 carbon atoms said substituents R, $R_1$, $R_4$ and $R_5$ chosen such that the resulting nucleus is of the silver halide sensitizing type; and Q represents the non-metallic atoms required to complete a silver halide sensitizing heterocyclic nucleus of the type used in merocyanine dyes containing from 5 to 6 atoms in the heterocyclic ring.

* * * * *